United States Patent [19]

Frey

[11] 4,272,855
[45] Jun. 16, 1981

[54] ANCHORING SURFACE FOR A BONE IMPLANT

[75] Inventor: Otto Frey, Winterthur, Switzerland

[73] Assignee: Sulzer Brothers Limited, Winterthur, Switzerland

[21] Appl. No.: 37,752

[22] Filed: May 10, 1979

[30] Foreign Application Priority Data

May 19, 1978 [CH] Switzerland .................... 5443/78

[51] Int. Cl.³ ............................................. A61F 1/03
[52] U.S. Cl. ...................................... 3/1.9; 128/92 C
[58] Field of Search ....................... 3/1.9, 1.91, 1.911, 3/1.912, 1.913; 128/92 C, 92 CA

[56] References Cited

U.S. PATENT DOCUMENTS 3,855,638  12/1974  Pilliar .......................... 128/92 C X

FOREIGN PATENT DOCUMENTS 837294  4/1952  Fed. Rep. of Germany ..... 128/92 CA
2659916  11/1977  Fed. Rep. of Germany .

OTHER PUBLICATIONS

"Further Experimental and Clinical Experience With Aluminum Oxide Endoprostheses", by Salzer et al., *J. Biomed. Mater. Res.*, vol. 10, pp. 847–856 (1976).

*Primary Examiner*—Clifford D. Crowder
*Attorney, Agent, or Firm*—Kenyon & Kenyon

[57] ABSTRACT

The anchoring surface of the bone implant is provided with villi (depressions or projections) devoid of corners and edges. The villi are of generally conical shape with transition surfaces merging into the base level of the anchoring surface. The villi allow implanting in a bone without cement since bone tissue is allowed to grow into or around the villi.

12 Claims, 4 Drawing Figures

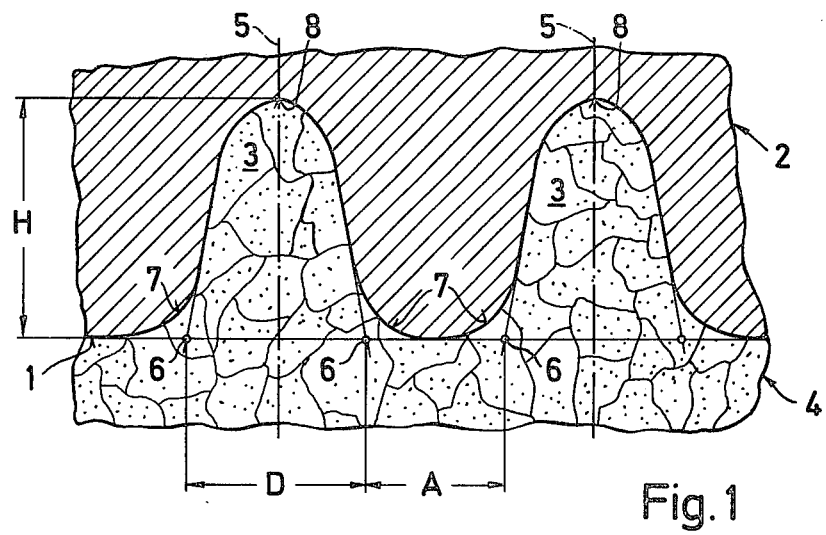
Fig.1
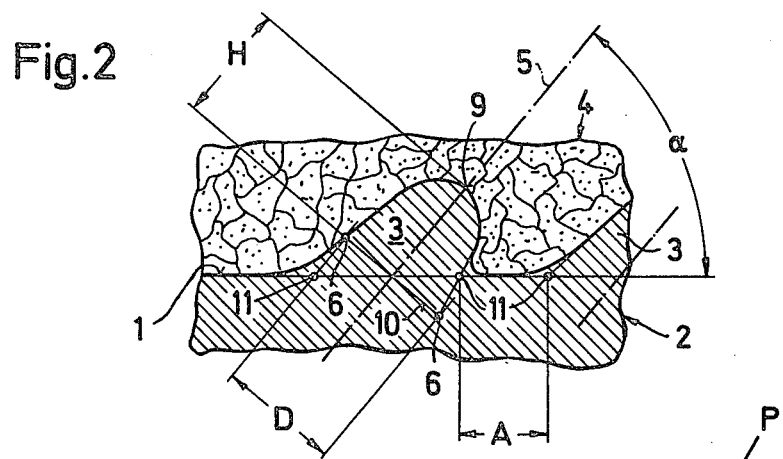
Fig.2
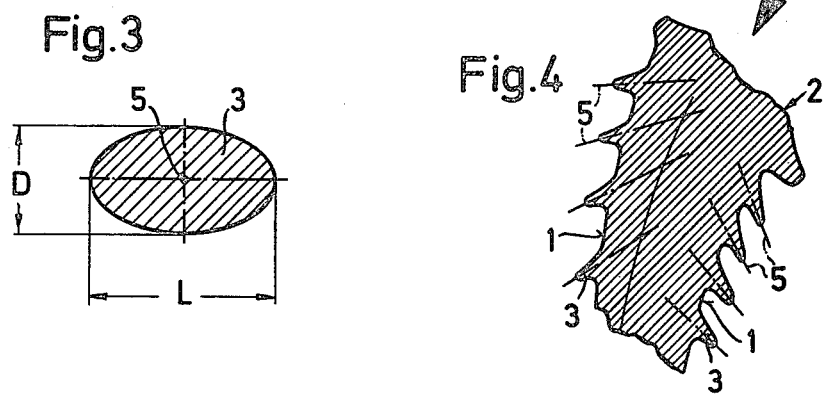
Fig.3
Fig.4

ANCHORING SURFACE FOR A BONE IMPLANT

This invention relates to a bone implant and, more particularly, to an anchoring surface for a bone implant.

Heretofore, it has been known to anchor surgical implants in bones with the use of cements. It has also been known to improve the anchorage of an implant without using a cement by constructing the implant so as to receive an ingrowth of bone tissue. For example, implants have been provided with porous surface of a certain depth such as described in U.S. Pat. Nos. 3,314,420 and 3,855,638. However, these porous surface implants have not proven themselves in practice since the mechanical strength of the anchoring surface is greatly affected in an adverse sense. The reason for this weakening of the material is that the pores produce sharp corners and edges in the material. This leads, especially in the case of longterm alternating stresses, to cracks which continue into the solid core of the implant and eventually to fatigue fractures.

Implants have also been constructed with a regular arrangement of bosses and/or depressions, such as described in German Pat. No. 837,294, in order to improve adhesion within bones. However, quite apart from the fact that sharp corners and edges have not been avoided in these structures, decisively increased adhesion between the implants and the tissue has not been achieved. This latter failure has occurred because only an insufficient increase of the surface is obtained. As is known, an increase in the anchoring surface is a decisive feature which can influence and improve a bond between the tissue and the anchoring part of the implant which acts as a foreign body therein.

Accordingly, it is an object of the invention to provide an anchoring surface for a bone implant which can optimize the growth of bone tissue without adversely effecting the mechanical strength of the anchoring surface.

It is another object of the invention to provide a bone implant with an improved anchoring surface.

Briefly, the invention provides a bone implant with an anchoring surface including a plurality of villi. Each villus has a generally conical shape devoid of corners and edges as well as a longitudinal axis which extends from a base level of the anchoring surface at an angle of from 50° to 90°. Each villus also has a transition surface merging into the base level of the anchoring surface without corners and edges.

The cross-section of each villus in a transverse plane at the base level has a transverse width D and a longitudinal length L in the range $D \leq L \leq 3D$. The height of each villus from the base level is in the range of $1D \leq H \leq 5D$. Also, the spacing A between the generatrices of the conical shape of adjacent villi in the transverse plane at the base level is in the range $0.25 D \leq A \leq D$.

By shaping the villi and forming their transitions into the anchoring surface in the above manner, the entire structure can be made without corners and edges and therefore has no fault locations with high stress peaks which lead to the cracks mentioned above and their consequences. In addition, the relationships between the transverse dimensions, height and spacing of the villi (this, of course, does not apply to the undisturbed zones at the outer regions of the structure) provide a considerable increase in the surface area available to ongrowing tissue. Furthermore, the surface structure of the implant thereby approaches the structure of a spongy tissue and has a shape similar to the spongy tissue. Such an approximation can be particularly promoted and the optimization of the structure as well as of the anchoring can be perfected, if the height of the villi corresponds to at least two-times the transverse width and the spacing of the villi corresponds at most to the transverse width.

To further match the surface structure to the natural growth, especially of the spongy bone tissue the growth of which is oriented, as is well known, by the local direction of the force and stress, the longitudinal axis of the villi can be arranged perpendicular to the direction of the local stress as far as is possible. In the case of villi with different longitudinal and transverse dimensions, the large side of the villus surface is arranged at right angles to the direction of the local stress.

The anchoring surface is applicable to all bone implants including hip joints, and to all metallic or ceramic materials as well as plastics customary in implant technology. The anchoring surface can be produced in various ways, for instance, by embossing or by appropriate design of the cavity of a casting mold as well as, in some circumstances, by chemical etching or also by milling or another mechanical kind of machining.

These and other objects and advantages of the invention will become more apparent from the following detailed description and appended claims taken in conjunction with the accompanying drawings in which:

FIG. 1 illustrates a greatly magnified cross-section of a portion of the anchoring surface of an implant according to the invention, into the villi of which, shaped as depressions, bone tissue has grown;

FIG. 2 illustrates a cross-sectional view of a raised villus which forms an angle ≠90° to the base level of the anchoring surface in accordance with the invention;

FIG. 3 illustrates a cross-section through a villus according to the invention with different longitudinal and transverse dimensions; and FIG. 4 illustrates a cross-section of the shank of a hip joint prothesis with locally different directions of the individual villus axes in accordance with the invention.

Referring to FIG. 1, the bone implant 2 has an anchoring surface into which individual villi 3 are worked as depressions with grown-in bone tissue 4 disposed in these depressions 3. While each villus 3 can have any cross-section, the cross-section preferably has the shape of a circle, an ellipse or an oval, the shorter of the cross-section dimensions (FIG. 3) being designated with D and, if applicable, the longer one with L.

Each villus 3 has a generally conical shape which is devoid of corners and edges. As indicated, the base or bottom 8 of each depression which forms a villus 3 is smoothly rounded. Each villus 3 also has a longitudinal axis 5 which extends from the base level 1 of the anchoring surface at an angle of from 50° to 90°. As shown, the axis 5 is at a 90° angle to the base level 1.

Each villus 3 also has a transition surface 7 which merges into the base level 1 without corners and edges. The cross-section of a villus 3 in a transverse plane at the base level 1 (see FIG. 3) has a transverse width D and a longitudinal length L in the range $D \leq L \leq 3D$. The transverse width D is determined as the distance between the intersections 6 of the basic conical form of the villus 3 with the base level 1 or with a plane 10 normal to the villus axis 5 by the intersection of the level 1 with the axis 5 (FIG. 2). This width D is the base dimension of the villus 3; all other dimensions are referenced thereto. Depending on the size of the anchoring surface and the loads to be taken up, the absolute value of the width D can assume values between 0.25 and 10 millimeters (mm).

The height H of each villus 3 from the base level 1 is in the range $1D \leq H \leq 5D$. For example, as shown in in FIG. 1 the height H is 1.3D. The spacing A between the generatrices of the conical shape of adjacent villi 3 in the transverse plane at the base level 1 is in the range $0.25 D \leq A \leq D$. As shown in FIG. 1, the spacing A is about 0.75 D except for the outer zones of the anchoring surface, which need not always extend over the entire anchoring area.

Referring to FIG. 2, where the villi 3 are disposed on a longitudinal axis 5 which is at an angle to the base level 1, e.g. 50° as shown, the transverse width D is the shortest distance of two intersections 6 and 11 of a villus 3 in the base level 1.

Again referring to FIG. 2, each villus 3 may be in the form of a projection which projects from the base level 1 of the anchoring surface. In this embodiment, the base level 1 is the base of the implant core 2. Further, the axis 5 of the villus 3 is directed perpendicularly to the local principal stress direction as far as possible.

Referring to FIG. 4, a hip joint prosthesis shank 2 is provided with a plurality of villi 3 with the axes 5 of the villi 3 disposed as a function of the local load direction which can definitely be different from the resultant load direction P and can form different angles with the base level 1.

As the two longitudinal cross sections of FIGS. 1 and 2 show, the transitions 7 of the villi 3 into the base level 1 as well as their "bottom" 8 (FIG. 1) and their "peak" 9 (FIG. 2) are without corners and edges and are realized by curves with relatively large radii of curvature. This prevents weakening of the mechanical strength of the implant material which may otherwise be caused by edge - and notch-shaped corners as described at the outset.

Regarding the choice of the magnitudes D, L, H, A within the limitations given, it is noted that this choice must be made so that (of course, within the possibilities given by the material characteristics of the implant material to be anchored) the shear forces in the boundary surface essentially defined by the base level in the vicinity of the bone material and in the vicinity of the implant material are to be matched to each other to the extent possible or, in the case of materials with material characteristics similar to the bone material, even be compensated to the extent possible.

What is claimed is:

1. A bone implant having an anchoring surface including a plurality of villi, each said villus having a generally conical shape devoid of corners and edges and a longitudinal axis extending from a base level of said surface at an angle of from 50° to 90°, each said villus having a transition surface merging into said base level of said anchoring surface without corners and edges, each said villus having a cross-section in a transverse plane at said base level with a transverse width D and a longitudinal length L in the range of $D \leq L \leq 3D$, a height H from said base level in the range $1D \leq H \leq 5D$, and with a spacing A between the generatrices of the conical shape of adjacent villi in said transverse plane in the range $0.25 D \leq A \leq 1D$.

2. An implant as set forth in claim 1 wherein said longitudinal axis of a villus is directed perpendicularly to the local stress direction.

3. An implant as set forth in claim 1 wherein a villus having a longitudinal length L greater than a transverse width D thereof has said longitudinal axis directed perpendicularly to the local stress direction.

4. An implant as set forth in claim 1 wherein a villus having a longitudinal length L greater than a transverse width D thereof has a height H at least equal to said longitudinal length L.

5. An implant as set forth in claim 1 wherein a villus has a height H at least equal to twice said transverse width D thereof.

6. An implant as set forth in claim 1 wherein each villus is a depression in said anchoring surface.

7. An implant as set forth in claim 1 wherein each villus is a projection.

8. An implant as set forth in claim 1 wherein said width is between 0.25 and 10 millimeters.

9. A bone implant having an anchoring surface including a plurality of villi, each said villus having a generally conical shape devoid of corners and edges and a longitudinal axis extending from a base level of said surface at an angle of from 50° to 90°, each said villus having a transition surface merging into said base level of said anchoring surface without corners and edges, each said villus having a cross-section in a transverse plane at said base level with a transverse width D and a longitudinal length L in the range of $D \leq L \leq 3D$, a height H from said base level in the range $D \leq H \leq 5D$, and with a spacing A between the generatrices of the conical shape of adjacent villi in said transverse plane in the range $0.25 D \leq A \leq 3D$.

10. A bone implant having an anchoring surface including a plurality of villi, each said villus having a generally conical shape devoid of corners and edges and a longitudinal axis extending from a base level of said surface at an angle of from 50° to 90°, each said villus having a transition surface merging into said base level of said anchoring surface without corners and edges, each said villus having a cross-section in a transverse plane at said base level with a transverse width D and a longitudinal length L in the range $D \leq L \leq 3D$, a height H from said base level in the range of $0.5 D \leq H \leq 5D$, and with a spacing A between the generatrices of the conical shape of adjacent villi in said transverse plane at most equal to said transverse width D.

11. A bone implant having an anchoring surface including a plurality of villi, each said villus having a generally conical shape devoid of corners and edges and a longitudinal axis extending from a base level of said surface at an angle of from 50° to 90°, each said villus having a transition surface merging into said base level of said anchoring surface without corners and edges, each said villus having a cross-section in a transverse plane at said base level with a transverse width D and a longitudinal length L in the range of $D \leq L \leq 3D$, a height H from said base level of 1.3 D, and with a spacing A between the generatrices of the conical shape of adjacent villi in said transverse plane of 0.75 D.

12. A bone implant having an anchoring surface including a plurality of villi, each said villus having a generally conical shape devoid of corners and edges and a longitudinal axis extending from a base level of said surface at an angle of from 50° to 90°, each said villus having a transition surface merging into said base level of said anchoring surface without corners and edges, each said villus having a cross-section in a transverse plane at said base level with a transverse width D and a longitudinal length L in the range of $D \leq L \leq 3D$, a height H from said base level in the range $0.5 D \leq H \leq 5D$, and with a spacing A between the generatrices of the conical shape of adjacent villi in said transverse plane in the range $0.25 D \leq A \leq 3D$.

* * * * *